United States Patent [19]

Holloway et al.

[11] Patent Number: 5,254,775
[45] Date of Patent: Oct. 19, 1993

[54] CHEMICAL PROCESS

[75] Inventors: John H. Holloway, Stoneygate; Eric G. Hope, Rugby; Paul J. Townson, Preston; Richard L. Powell, Tarporley, all of England

[73] Assignee: Imperial Chemical Industries PLC, London, England

[21] Appl. No.: 849,603

[22] Filed: Mar. 12, 1992

[30] Foreign Application Priority Data

Mar. 12, 1991 [GB] United Kingdom ............... 9105166

[51] Int. Cl.$^5$ .............................................. C07C 17/20
[52] U.S. Cl. .................................................. 570/170
[58] Field of Search ...................... 570/168, 170, 169

[56] References Cited

U.S. PATENT DOCUMENTS

| | | | |
|---|---|---|---|
| 3,660,307 | 5/1972 | Scherer et al. | 570/188 |
| 3,752,850 | 8/1973 | Scherer et al. | 570/188 |
| 4,081,487 | 3/1978 | Anello et al. | |
| 4,110,406 | 8/1978 | Anello et al. | |
| 4,110,407 | 8/1978 | Anello et al. | |
| 4,110,408 | 8/1978 | Anello et al. | |
| 4,264,530 | 4/1981 | Ohsaka et al. | |
| 4,578,369 | 3/1986 | Muller et al. | 570/170 |

FOREIGN PATENT DOCUMENTS 2756292 6/1978 Fed. Rep. of Germany .
823519 11/1959 United Kingdom .

Primary Examiner—Alan Siegel
Attorney, Agent, or Firm—Cushman, Darby & Cushman

[57] ABSTRACT

A process for the preparation of an alkane containing fluorine which process comprises contacting a halogenated alkane containing at least one halogen atom selected from chlorine, bromine and iodine with a transition metal oxide fluoride and replacing at least one chlorine, bromine or iodine atom in said halogenated alkane by a fluorine atom.

The transition metal oxide fluoride may be an oxide fluoride of vanadium, molybdenum, tungsten, rhenium or osmium, and the replacement of halogen atom in the starting halogenated alkane is highly selectove where the starting halogenated alkane also contains hydrogen.

7 Claims, No Drawings

CHEMICAL PROCESS

This invention relates to a process for the fluorination of aliphatic compounds and more particularly to a process for the replacement by fluorine of at least one halogen atom other than fluorine in aliphatic compounds.

It is already known to manufacture aliphatic compounds containing fluorine by reacting aliphatic chlorocarbons or chlorohydrocarbons with fluorinating agents such as antimony pentafluoride. In many cases, however, known fluorinating agents do not give entirely satisfactory results, being somewhat deficient in activity and/or in product selectivity.

It has now been found that transition metal oxide fluorides (oxyfluorides) are useful fluorinating agents capable of replacing by fluorine one or more other halogen atoms in aliphatic compounds, the replacement being highly selective when hydrogen is also present in the starting aliphatic compound.

According to the present invention there is provided a process for the preparation of an alkane containing fluorine which process comprises contacting a halogenated alkane containing at least one halogen atom selected from chlorine, bromine and iodine with a transition metal oxide fluoride and replacing at least one chlorine, bromine or iodine atom in said halogenated alkane by a fluorine atom.

Halogenated alkanes which may be employed in the process of the invention may contain one or more carbon atoms, for example, typically up to 6 carbon atoms, and have at least one replaceable halogen atom selected from chlorine, bromine and iodine. Other atoms, for example hydrogen or fluorine may also be present, indeed the use of the transition metal oxyfluorides in the process of the present invention are particularly useful where the halogenated alkane also contains hydrogen as they provide highly selective replacement of fluorine for halogen.

Especially useful starting materials include hydrochlorocarbons, chlorocarbons, chlorofluorocarbons and chlorofluorohydrocarbons, especially hydrochlorocarbons and chlorofluorohydrocarbons.

Specific examples of halogenated alkanes which may be used include dichloromethane, chloroform, carbon tetrachloride, chlorofluoromethane, dibromomethane, bromofluoromethane and 1-chloro-2,2,2-trifluoroethane, from which the products may be respectively difluoromethane, and 1,1,1,2-tetrafluoroethane.

Transition metal oxide fluorides which may be used in the method of the invention particularly include the oxide fluorides of vanadium, molybdenum, tungsten, rhenium and osmium, for example $VOF_3$, $MoOF_4$, $WOF_4$, $ReOF_4$, $ReOF_5$, $OsO_3F_2$, $OsO_2F_3$, $OsOF_5$ and $OsOF_4$, and especially the oxide fluorides of molybdenum rhenium and osmium, particularly $MoOF_4$, $ReOF_4$, $OsO_3F_2$ and $OsO_2F_3$.

In operating the method of the invention, the halogenated alkane may be contacted with the transition metal oxide fluoride at a temperature at which the halogenated alkane is in the liquid phase or the vapour phase, but conveniently the liquid phase. Accordingly the temperature may be from about $-80°$ C. to about $25°$ C., depending upon the boiling point of the halogenated alkane, although the reaction proceeds, and may be conducted at, temperatures higher than $25°$ C., for example up to $100°$ C., in which case the halogenated alkane may be in the vapour phase. The process of the invention is preferably operated under substantially anhydrous conditions and is conveniently operated at about atmospheric pressure although superatmospheric or subatmospheric pressures may be employed if desired.

The proportions of halogenated alkane and transition metal oxide fluoride are not critical; either may be in excess over stoichiometric, if desired. Thus, for example, the proportion of halogenated alkane to transition metal oxide fluoride may be in the range from about 50:1 to about 1:50 and preferably from about 20:1 to about 1:20 of the stoichiometrically required proportion, although these ranges are given merely by way of guidance and are in no way limiting on the process of the present invention. Hydrogen fluoride may also be included in the reaction mixture as a fluorinating agent, the oxide fluoride then optionally being employed in a catalytic amount.

The transition metal oxide fluoride may, depending on the reaction temperature, be present as a solid or vapour in the reaction vessel and way be supported on a substrate, for example aluminium fluoride or carbon.

The invention is illustrated by the following examples in which the organic materials were handled in a vacuum line made from stainless steel tubing with stainless steel valves and the metal oxide fluorides were handled in satellite lines made from PTFE. Reactions were conducted in FEP tubes (copolymer of hexafluoropropylene and TFE) which could be sealed thermally in a small ring furnace after reaction had reached completion and could be inserted into a standard precision 5 mm n.m.r. glass tube with a thin film of the lock substance - $d_6$ acetone, placed between the tubes. To obtain a reliable integration of $^1H$ against $^{19}F$ signals, $CF_3CH_2OH$ ( 33% v/v) was added to the lock substance. All equipment was seasoned with fluorine gas at a pressure of 700-800 mbar for about 16 hours.

The transition metal oxide fluorides were prepared by conventional methods and were stored in $F_2$- passivated Ni cylinders prior to use.

The products were analysed by n.m.r. spectroscopy on a Bruker FT spectrometer AM 300 ($^1H$ at 300.0 MHz, $^{19}F$ at 282.4 MHz) with a 5 mm bore selective probe.

EXAMPLE 1.

Fluorination of $CH_2Cl_2$ by $OsOF_5$

A 15 cm long $\times$ 4 mm diameter (outside diameter) $\times$ 0.55 mm wall thickness FEP tube was connected via a PTFE valve (supplied by Production Techniques) to an all metal vacuum line, evacuated to $<10^{-5}$ Torr, passivated with $F_2$ gas (400 Torr) for 20 minutes, and re-evacuated. The valve was closed and the weight of the valve and tube measured.

52.1 mg (0.173 mmol) of $OsOF_5$ (prepared as described in J.Chem.Physics., 1971, 54, 4305.) was condensed from the nickel storage cylinder into the pre-fluorinated FEP tube by vacuum transfer at $-196°$ C. as follows. The Ni storage container and FEP tube were connected to the vacuum line. The connections were evacuated, passivated with $F_2$ gas and re-evacuated. The FEP tube was cooled to $-196°$ C. in liquid nitrogen and the valves to the FEP tube and Ni storage container were opened to allow the $OsOF_5$ to sublime into the FEP tube. The valve to the storage container was closed and the apparatus was re-evacuated after which the valve to the FEP tube was closed and the FEP tube was allowed to warm to room temperature. The FEP tube and valve were taken off the vacuum line and re-weighed.

The FEP tube containing $OsOF_5$ and a glass storage vessel containing dried $CH_2Cl_2$ were connected to the vacuum line via a PTFE T-piece. The connectors and T-piece were evacuated, passivated with $F_2$ and re-evacuated.

384.2mg, 4.52 mmol of $CH_2Cl_2$ was sublimed into the FEP tube cooled to $-196°$ C. in liquid nitrogen. The PTFE valve was closed and the reaction mixture allowed to warm slowly to $-78°$ C. in a dry ice-acetone bath and then to room temperature (20° C.) with frequent shaking. The reaction was allowed to proceed for 1 hour.

The FEP tube and PTFE valve were taken off the vacuum line and re-weighed.

The FEP reaction tube and a second FEP tube were connected to the vacuum line via a PTFE T-piece, and the connectors and T-piece were evacuated, passivated with $F_2$ and re-evacuated. The second FEP tube was cooled to $-196°$ C. in liquid nitrogen, the PTFE valves opened and the volatile product from the reaction tube was allowed to sublime into the second FEP tube. The involatile precipitate in the reaction tube was taken for elemental analysis.

The FEP tube containing the volatile product was kept cold at $-196°$ C. and was then placed in a small ring furnace and heated gently to form a vacuum and pressure tight seal. The n.m.r. spectra of the volatile product was determined at 298K.

The results are shown in Table 1. From these results it was calculated that the replacement of chlorine by fluorine was 92% selective.

EXAMPLE 2

Fluorination of $CH_2Cl_2$ by $ReOF_5$

The procedure described in example 1 was followed except that 73.1 mg, 0.268 mmol of $ReOF_5$ (prepared as described in J.Chem,Physics., 1971, 54, 4305.) and 437.7 mg, 5.15 mmol of $CH_2Cl_2$ were sublimed into the reaction tube. The reaction was allowed to proceed for 3 days before n.m.r. analysis was carried out. The involatile product was determined to be $ReOCl_4$.

The results are shown in Table 1. From these results it was calculated that the replacement of chlorine by fluorine was 85% selective.

EXAMPLE 3

Fluorination of $CH_2Cl_2$ by $ReOF_4$

The procedure described in example 1 was followed except that 37.8 mg, 0.136 mmol of solid $ReOF_4$(prepared as described in J.Chem. Soc. Dalton Trans., 1981, 1212) was loaded into the pre-fluorinated weighed FEP tube in a dry box (<1 ppm $H_2O$ supplied by Vacuum Atmospheres Ltd) and 818. 5 mg, 9. 63 mmol of $CH_2Cl_2$ were sublimed into the reaction tube. The involatile product was determined to be $ReOCl_4$.

The results are shown in Table 1. From these results it was calculated that the replacement of chlorine by fluorine was 99% selective and that the total yield of organic products was 100%.

EXAMPLE 4

Fluorination of $CH_2Cl_2$ by $OsO_3F_2$

The procedure described in example 1 was followed except that 31.48 mg, 0.114 mmol of solid $OsO_3F_2$ (prepared as described in J.Chem. Soc., Dalton Trans., 1968, 61) was loaded into the pre-fluorinated weighed FEP tube in a dry box (<1ppm $H_2O$ supplied by Vacuum Atmospheres Ltd) and 503.8 mg, 5.93 mmol of $CH_2Cl_2$ were sublimed into the reaction tube.

The results are shown in Table 1. From these results it was calculated that the replacement of chlorine by fluorine was 93% selective.

EXAMPLE 5

Fluorination of $CH_2Cl_2$ by $OsO_2F_3$

The procedure described in example 1 was followed except that 48.0 mg, 0.172 mmol of solid $OsO_2F_3$ (prepared as described in J.Chem. Soc. Dalton Trans., 1988, 997) was loaded into the pre-fluorinated weighed FEF tube in a dry box (<1ppm $H_2O$ supplied by Vacuum Atmospheres Ltd) and 706.3 mg, 8.31 mmol of $CH_2Cl_2$ were sublimed into the reaction tube.

The results are shown in Table 1. From these results it was calculated that the replacement of chlorine by fluorine was 99% selective and that the total yield of organic products was 98.3%.

EXAMPLE 6

Fluorination of $CH_2Br_2$ by $ReOF_5$

The procedure described in example 1 was followed except that 156.31 mg, 0.526 mmol of $ReOF_5$ and 922.2 mg, 5.30 mmol of $CH_2Br_2$ were sublimed into the reaction tube. The reaction was allowed to proceed for 3 days before n.m.r. analysis was carried out. The involatile product was determined to be $ReOBr_4$/$ReOBr_3$.

The results are shown in Table 2. From these results it was calculated that the replacement of bromine by fluorine was 99.5% selective.

EXAMPLE 7

Fluorination of $CH_2Br_2$ by $OsOF_5$

The procedure described in example 1 was followed except that 14.2 mg, 0.047 mmol of $OsOF_5$ and 816.6 mg, 4.7 mmol of $CH_2Br_2$ were sublimed into the reaction tube.

The results are shown in Table 2. From these results it was calculated that the replacement of bromine by fluorine was 100% selective.

EXAMPLE 8

Fluorination of $CH_2Br_2$ by $ReOF_4$

The procedure described in example 1 was followed except that 37.8 mg, 0.136 mmol of solid $ReOF_4$ was loaded into the pre-fluorinated weighed FEP tube in a dry box (<1ppm $H_2O$ supplied by Vacuum Atmospheres Ltd) and 1053.2 mg, 6.06 mmol of $CH_2Br_2$ were sublimed into the reaction tube. The involatile product was determined to be $ReOBr_3$/$ReOBr_4$.

The results are shown in Table 2. From these results it was calculated that the replacement of bromine by fluorine was 100% selective.

EXAMPLE 9

Fluorination of $CH_2Br_2$ by $OsO_3F_2$

The procedure described in example 1 was followed except that 14.5 mg, 0.056 mmol of solid $OsO_3F_2$ was loaded into the pre-fluorinated weighed FEP tube in a dry box (<1 ppm $H_2O$ supplied by Vacuum Atmospheres Ltd) and 1055.0 mg, 6.57 mmol of $CH_2Br_2$ were sublimed into the reaction tube.

The results are shown in Table 2. From these results it was calculated that the replacement of bromine by fluorine was 100% selective.

EXAMPLE 10

Fluorination of $CH_2Br_2$ by $OsO_2F_3$

The procedure described in example 1 was followed except that 56.9 mg, 0.204 mmol of solid $OsO_2F_3$ was loaded into the pre-fluorinated weighed FEP tube in a dry box (<1ppm $H_2O$ supplied by Vacuum Atmospheres Ltd) and 1276.9 mg, 7.35 mmol of $CH_2Cl_2$ were sublimed into the reaction tube.

The results are shown in Table 2. From these results it was calculated that the replacement of bromine by fluorine was 100% selective.

EXAMPLE 11

Fluorination of $CH_2Br_2$ by $MoOF_4$

The procedure described in example 1 was followed except that 69.0 mg, 0.367 mmol of solid $MoOF_4$ (prepared as described in J,Chem. Soc., Dalton Trans., 1981, 1212) was loaded into the pre-fluorinated weighed FEP tube in a dry box (<1ppm $H_2O$ supplied by Vacuum Atmospheres Ltd) and 997.6 mg, 5.74 mmol of $CH_2Br_2$ were sublimed into the reaction tube. The reaction was allowed to proceed for 14 days before m.m.r. analysis was carried out. The involatile product was determined to be $MoOBr_4$.

The results are shown in Table 2. From these results it was calculated that the replacement of bromine by fluorine was 100% selective.

EXAMPLE 12

Fluorination of $CH_2Br_2$ by $WOF_4$

The procedure described in example 1 was followed except that 77.5 mg, 0.281 mmol of solid $WOF_4$ (prepared as described in J,Chem. Soc., Dalton Trans., 1981, 1212) was loaded into the pre-fluorinated weighed FEP tube in a dry box (<1ppm $H_2O$ supplied by Vacuum Atmospheres Ltd) and 839.4 mg, 4.83 mmol of $CH_2Br_2$ were sublimed into the reaction tube. The reaction was allowed to proceed for 14 days before n.m.r. analysis was carried out. The involatile product was determined to be $WOBr_4$.

The results are shown in Table 2. From these results it was calculated that the replacement of bromine by fluorine was 89% selective.

TABLE 1

PRODUCTS OF FLUORINATION OF $CH_2Cl_2$.

| PRODUCTS MOLE %. (No. of mmoles). | TM OXIDE FLUORIDE. | | | | |
|---|---|---|---|---|---|
| | $ReOF_5$. | $ReOF_4$. | $OsO_3F_2$. | $OsO_2F_3$. | $OsOF_5$. |
| $CH_2ClF$ | 77.0 | 97.5 (0.52) | 84.0 | 85.5 (0.385) | 84.7 |
| $CH_2F_2$. | 3.5 | 1.8 (0.008) | 10.5 | 13.5 (0.061) | 7.2 |
| $CHCl_2F$ | 1.5 | 0.5 (0.003) | 5.5 | 0.3 | 6.4 |
| $CHF_3$. | 6.7 | | | 0.6 | 6.7 |
| $CF_2Cl_2$. | | 0.2 | | | 0.2 |

TABLE 2

PRODUCTS OF FLUORINATION OF $CH_2Br_2$.

| METAL OXIDE FLUORIDE. | PRODUCT/MOLE % (No. of mmoles). | | |
|---|---|---|---|
| | $CH_2BrF$ | $CH_2F_2$ | $CHBr_2F$. |
| $MoOF_4$. | 22.8 | 77.2 | |
| $WOF_4$. | 62.7 | 26.5 | 10.7 |
| $ReOF_4$. | 65.3 | 34.7 | |
| $ReOF_5$. | 89.4 | 10.1 | 0.5 |
| $OsOF_5$. | 77.2 | 22.8 | |
| $OsO_3F_2$. | 91.9 | 8.9 | |
| $OsO_2F_3$. | 71.7 (1.51) | 28.3 (0.599) | |

We claim:

1. A process for the preparation of an alkane containing fluorine which process comprises contacting a halogenated alkane containing at least one halogen atom selected from chlorine, bromine and iodine with a transition metal oxide fluoride which is an oxide fluoride of molybdenum, rhenium and osmium whereby to replace at least one chlorine, bromine or iodine atom in said halogenated alkane by a fluorine atom.

2. A process as claimed in claim 1 in which the alkane containing at least one halogen atom selected from chlorine, bromine and iodine comprises a hydrochlorocarbon, chlorocarbon, chlorofluorocarbon or chlorofluorohydrocarbon having from between 1 and 6 carbon atoms.

3. A process as claimed in claim 1 in which the halogenated alkane is selected from the group consisting of dichloromethane, chloroform, carbon tetrachloride, chlorofluoromethane, dibromomethane, bromofluoromethane and 1-chloro-2,2,2-trifluoroethane.

4. A process as claimed in claim 1 in which the transition metal oxide fluoride is selected from the group consisting of $MoOF_4$, $ReOF_4$, $ReOF_5$, $OsO_3F_2$, $OsO_2F_3$, $OsOF_5$ and $OsOF_4$.

5. A process as claimed in claim 1 in which the transition metal oxide fluoride is selected from the group consisting of $MoOF_4$, $ReOF_4$, $OsO_3F_2$ and $OsO_2F_3$.

6. A process as claimed in claim 1 which comprises contacting the transition metal oxide fluoride with the halogenated alkane in the liquid or vapour phase at a temperature in the range from about $-80°$ C. to about $100°$ C.

7. A process as claimed in claim 6 in which the proportion of halogenated alkane to transition metal oxide fluoride is in the range from about 20:1 to about 1:20.

* * * * *